United States Patent [19]

Straw

[11] Patent Number: 5,015,465

[45] Date of Patent: May 14, 1991

[54] ORAL HYGIENE COMPOSITIONS

[75] Inventor: Philip L. Straw, Woodham, England

[73] Assignee: Beecham Group P.L.C., England

[21] Appl. No.: 210,834

[22] Filed: Jun. 24, 1988

Related U.S. Application Data

[63] Continuation of Ser. No. 842,490, Mar. 21, 1986, abandoned.

[30] Foreign Application Priority Data

Mar. 23, 1985 [GB] United Kingdom ............ 8507625
Jun. 12, 1985 [GB] United Kingdom ............ 8514860

[51] Int. Cl.$^5$ .................................. A61K 7/18
[52] U.S. Cl. .................................. 424/052; 424/49; 424/58
[58] Field of Search ................. 424/49, 52, 58

[56] References Cited

U.S. PATENT DOCUMENTS 3,122,483  2/1964  Rosenthal ............ 424/49
4,011,309  3/1977  Lutz .................. 424/49
4,367,219  1/1983  Schole ................ 424/52

FOREIGN PATENT DOCUMENTS

0079611A3  5/1983  European Pat. Off. .
7601870    8/1977  Netherlands .

OTHER PUBLICATIONS

Jefopoulos, *Dentifrices*, Noyes Data Corp., Park Ridge, N.J., pp. 79-81, 1970.
Translation of Netherlands Patent No. 7,601,870.
Addy et al., J. Clin. Period., 1983, 10, pp. 351-363.

Primary Examiner—Ronald W. Griffin
Attorney, Agent, or Firm—Jacobs & Jacobs

[57] ABSTRACT

An oral hygiene composition comprising a silica base, from 1 to 10% by weight of the composition of a water soluble non-toxic strontium salt, a fluoride source providing from 250 ppm to 2000 ppm of fluoride in the composition, and a dentally acceptable carrier, provided that when the strontium salt is other than strontium acetate the silica base has a BET surface area of from 50 to 400 m$^2$/g.

The composition has improved anti-sensitivity properties coupled with high levels of available fluorine.

8 Claims, No Drawings

ORAL HYGIENE COMPOSITIONS

CROSS-REFERENCE

This is a continuation of Ser. No. 842,490 filed Mar. 21, 1986, now abandoned.

The present invention relates to oral hygiene compositions, and in particular to compositions for the treatment of dentine hypersensitivity.

The symptoms of hypersensitive dentine are fairly widespread, and various toothpaste formulations have hitherto been proposed to deal with the problem. For example, UK Patent Specification No 990957 discloses the use of strontium salts in toothpaste compositions, these salts being relatively non-toxic and non-injurious to mouth tissues. One of the disadvantages of strontium salt containing compositions is that such salts are incompatible with fluorides due to the reaction between strontium and fluoride ions to form insoluble strontium fluoride. This means that the anti-caries benefit of fluoride cannot be achieved with a strontium-salt containing toothpaste. It has now been found that high levels of available fluoride ions and strontium ions can be obtained when a water soluble strontium salt is used together with a silica base of particular particle size range as the dentally acceptable abrasive, or when strontium acetate is used with any silica base.

According to the present invention there is provided an oral hygiene composition comprising a silica base, from 1 to 10% by weight of the composition of a water soluble non-toxic strontium salt, a fluoride source providing from 250 ppm to 2000 ppm of fluoride in the composition, and a dentally acceptable carrier, provided that when the strontium salt is other than strontium acetate the silica base has a BET surface area of from 50 to 400, $m^2/g$; preferably from 100 to 300. As used in this specification and the appended claims, the term "BET" refers to the Braunauer-Emmett-Teller method of determining surface areas.

The preferred strontium salt is strontium acetate, but other examples which may be used include strontium chloride, strontium nitrate, strontium lactate and strontium bromide.

Preferably, the composition contains from 8 to 32% by weight of the composition, of silica base, which may have an abrasive silica component and a thickening silica component. The preferred amount of abrasive silica is from 5 to 20% by weight of the composition, and that of thickening silica is from 3 to 12% by weight. The silica abrasive can be a precipitated silica or a silica gel, such as the silica xerogels described in U.S. Pat. No. 3538230. Preferred precipitated silicas are those typically marketed under the tradename 'Zeodent' by the J. M. Huber Corporation and, 'Tixosil' by Rhone-Poulenc. 'Zeodent' has a BET surface area of about 150 to 250,$m^2/g$, and 'Tixosil' has a BET surface area of about 100 $m^2/g$.

Preferred thickening silicas are typically marketed under the trade name 'Sipernat' by Degussa (Frankfurt) and 'Syloid' by W. R. Grace and Company, Davison Chemical Division.

The preferred strontium salt, strontium acetate, is usually employed in the form of its hemihydrate, and the 1 to 10% by weight content in the composition of the invention refers to the weight of the component in this form. The preferred amount of strontium acetate hemihydrate is from 5 to 8% by weight.

The fluoride source in the composition of the invention may be an alkali-metal fluoride such as sodium, potassium or lithium fluoride, and the use of sodium fluoride is especially preferred. Other suitable fluorides include ammonium, stannous and zinc fluorides.

In addition to, or instead of, the above fluorides, the fluoride source may also comprise a monofluorophosphate, preferably an alkali metal monofluorophosphate. Sodium monofluorophosphate is especially preferred but the corresponding potassium and/or lithium salts can also be employed. Other suitable monofluorophosphates are those of formulae $Na_4P_3O_9F$; $K_4P_3O_9F$; $Na_3K_3O_9F$; $(NH_4)_3NaP_3O_9F$; and $Li_4P_3O_9F$.

The total amount of fluoride and/or monofluorophosphate used, and the weight ratio of these materials, is dependent to some extent on the type of oral hygiene composition, but it should be an effective, but non-toxic, amount. Preferably, the total amount of fluoride and/or monofluorophosphate is such as to provide from 500ppm to 1000ppm of fluorine in the composition.

The compositions of the invention may optionally contain other agents known to enhance the anticaries effect of fluoride and monofluorphosphate. For example, calcium glycerophosphate is known to enhance the anticaries effect of monofluorophosphate and may be incorporated in a weight ratio of up to 1:3, preferably 1:20 to 1:3, to the total weight of monofluorophosphate.

The compositions of the invention will also usually contain surfactants, gelling agents and other excipients such as flavouring and colouring agents.

The compositions of the invention are preferably presented in the form of a conventional toothpaste or dental powder formulation. The compositions may also be in the form of other oral hygiene compositions, for example, the ingredients may be incorporated into a mouthwash or into compositions which will be chewed by the user, for example, chewing gum, tablets, pastilles and lozenges. These compositions will contain the conventional base materials together with suitable flavours and sweetening agents and may be formulated in known manner.

Surfactants used in the composition of the invention are normally water-soluble, non-soap, or synthetic organic detergents. Particularly materials such as sodium N-methyl-N-cocyl laurate, which is marketed under the trade name Adinol CT by Croda. Other suitable surfactants include the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzenesulphonates); and higher alkyl sulphoacetates (for example sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid and valine, particularly the N-lauroyl, myristoyl and palmitoyl sarcosinate compounds.

The surfactants are generally present in an amount of 0.05 to 15%, preferably 0.05 to 5% by weight of composition.

In general, the liquids in the compositions of the invention will comprise chiefly water glycerine, sorbitol and/or a glycol, including suitable mixtures thereof.

Suitably, the glycol is propylene glycol or a polyethylene glycol. It is also preferred to use a gelling agent in toothpastes such as natural or synthetic gums or gum-like materials. Non-ionic gums such as guar gum or xanthan gum are particularly preferred since these help to preclude interaction with strontium, but other gums or gum-like materials, such as Irish Moss, gum tragacanth, sodium carboxymethylcellulose, polyvinylpyrrolindone or starch may be used. The gum content is usually up to 10% and preferably 0.01 to 5% by weight of the preparation.

Other materials may be added such as soluble saccharin, flavouring oils (e.g. oils of spearmint, wintergreen peppermint), chloroform, colouring or whitening agents (e.g. titanium dioxide), preservative (e.g. sodium benzoate), emulsifying agents, silicones, alcohol, menthol, chlorophyll compounds (e.g. sodium copper chlorophyllin), antibacterial agents (e.g. chlorhexidine), anti-plaque agents and anti-calculus agents.

This invention is now illustrated with reference to the following Examples.

EXAMPLES 1 and 2

Two toothpaste formulations were prepared having the following ingredients, the figures being % w/w.

|  | Example 1 | Example 2 |
|---|---|---|
| Glycerin | 24.00 | 24.00 |
| Saccharin (15% solution) | 2.80 | 2.80 |
| Sodium monofluorophosphate | 0.80 | 0.80 |
| Guar gum | 1.00 | 1.00 |
| Titanium dioxide | 1.00 | 1.00 |
| Abrasive silica (*Tixosil 53BE) | 14.00 | 12.00 |
| Thickening silica (**Sipernat 22 g) | 5.00 | 6.00 |
| Strontium acetate | 8.00 | 8.00 |
| Total preservatives | 0.10 | 0.10 |
| Detergent (***Adinol CT) | 2.00 | 2.00 |
| Flavour | 1.00 | 1.00 |
| Water | to 100.00 | to 100.00 |

*Trade Mark of Rhone - Poulenc
**Trade Mark of Degussa
***Trade Mark of Croda

EXAMPLE 3

The following formulation was prepared containing sodium fluoride in place of sodium monofluorophosphate.

|  | % w/w |
|---|---|
| Glycerin | 24.00 |
| Saccharin (15% solution:) | 2.80 |
| Sodium fluoride | 0.22 |
| Guar gum | 1.00 |
| Titanium dioxide | 1.00 |
| Abrasive silica (Tixosil 53BE) | 14.00 |
| Thickening silica (Sipernat 22S) | 5.00 |
| Strontium acetate | 8.00 |
| Total preservatives | 0.10 |
| Detergent (Adinol CT) | 2.00 |
| Flavour | 1.00 |
| Water | to 100.00 |

I claim:

1. An aqueous hygiene composition comprising a silica base, from 1 to 10% by weight of the composition of a water soluble non-toxic strontium salt selected from the group consisting of strontium acetate, strontium chloride, strontium nitrate, strontium lactate and strontium bromide, a fluoride source providing from 250 ppm to 2000 ppm of fluoride in the composition, and a dentally acceptable carrier comprising water, provided that when the strontium salt is other than strontium acetate the silica base has a BET surface area of from 50 to 400 m$^2$/g.

2. A composition according to claim 1, in which the BET surface area is from 100 to 300 m$^2$/g.

3. A composition according to claim 1, in which the silica base is present in an amount of from 8 to 32% by weight.

4. A composition according to claim 3, in which the silica base comprises precipitated silica or silica gel.

5. A composition according to claim 1, in which the fluoride source comprises an alkali metal fluoride, an alkali metal monofluorophosphate or a mixture thereof.

6. A composition according to claim 1, containing a non-ionic or low ionic surfactant.

7. A composition according to claim 1, containing a non-ionic gum as a gelling agent.

8. A composition according to claim 1, in which the strontium salt is strontium acetate.

* * * * *